(12) United States Patent
McCarthy et al.

(10) Patent No.: US 9,522,134 B2
(45) Date of Patent: Dec. 20, 2016

(54) COMPOUNDS

(71) Applicant: ORCA PHARMACEUTICALS LIMITED, Abingdon, Oxfordshire (GB)

(72) Inventors: Clive McCarthy, Oxfordshire (GB); Naomi Went, Oxfordshire (GB); Roine Inge Olsson, Mölndal (SE)

(73) Assignee: ORCA PHARMACEUTICALS LIMITED, Abingdon, Oxfordshire (GB)

( * ) Notice: Subject to any disclaimer, the term of this patent is extended or adjusted under 35 U.S.C. 154(b) by 0 days.

(21) Appl. No.: 15/074,656

(22) Filed: Mar. 18, 2016

(65) Prior Publication Data

US 2016/0199348 A1      Jul. 14, 2016

Related U.S. Application Data

(63) Continuation of application No. PCT/GB2015/053184, filed on Oct. 23, 2015.

(30) Foreign Application Priority Data

Oct. 24, 2014   (GB) .................................. 1419015.1

(51) Int. Cl.
| | | |
|---|---|---|
| *A61K 31/405* | (2006.01) | |
| *C07D 209/12* | (2006.01) | |
| *A61K 31/404* | (2006.01) | |
| *A61K 9/00* | (2006.01) | |

(52) U.S. Cl.
CPC ........... *A61K 31/404* (2013.01); *A61K 9/0053* (2013.01); *A61K 31/405* (2013.01); *C07D 209/12* (2013.01)

(58) Field of Classification Search
CPC ............................. A61K 31/405; C07D 209/12
USPC ............................................ 514/419; 548/469
See application file for complete search history.

(56) References Cited

FOREIGN PATENT DOCUMENTS

| | | |
|---|---|---|
| EP | 1837329 | 9/2007 |
| JP | 1100580 | 5/1986 |
| WO | WO 2006/050006 | 5/2006 |
| WO | WO 2006/075638 | 7/2006 |
| WO | WO 2009/005672 | 1/2009 |
| WO | WO 2012/024620 | 2/2012 |
| WO | WO 2012/106995 | 8/2012 |
| WO | WO 2014/026327 | 2/2014 |
| WO | WO 2014/026328 | 2/2014 |
| WO | WO 2014/026329 | 2/2014 |
| WO | WO 2014/026330 | 2/2014 |
| WO | WO 2014/028589 | 2/2014 |
| WO | WO 2014/028591 | 2/2014 |
| WO | WO 2014/028597 | 2/2014 |
| WO | WO 2014/028600 | 2/2014 |
| WO | WO 2015/036411 | 3/2015 |
| WO | WO 2015/087234 | 6/2015 |

OTHER PUBLICATIONS

Acton et al, Journal of Med. Chem. (2009), vol. 52, pp. 3846-3854.*
Acton et al, "Discovery of (2R)-2-(3-{3-[(4-methoxyphenyl)carbonyl]-2-methyl-6(trifluoromethoxy)-1H-indol-1-yl}phenoxy)butanoic acid (MK-0533): A novel selective peroxisome proliferator-activated receptor gamma modulator for the treatment of type 2 diabetes mellitus with a reduced potential to increase plasma and extracellular fluid volume" J. Med. Chem., 52, 3846-3854, (2009).
Fauber et al, "Discovery of [1,5-a]pyridines and pyrimidines as potent and selective RORc inverse agonists", Bioorganic & Medicinal Chemistry Letters, 25(1), 2907-2912 (Aug. 1, 2015).

* cited by examiner

*Primary Examiner* — Kamal Saeed
*Assistant Examiner* — Janet L Coppins
(74) *Attorney, Agent, or Firm* — Saul Ewing LLP; Domingos Silva; Kathryn Doyle

(57) ABSTRACT

The present invention relates to compounds of formula (I):

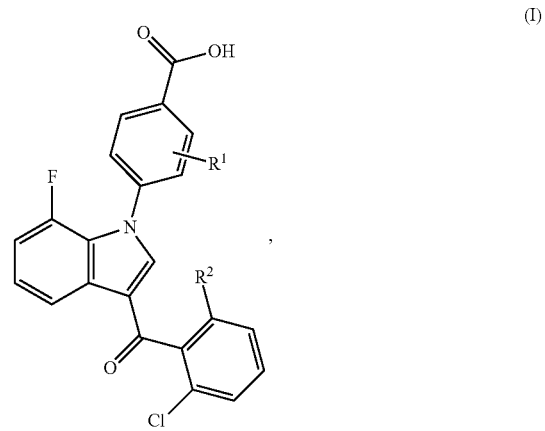

wherein $R^1$ and $R^2$ are as defined herein. In certain embodiments, the compounds of the present invention are inhibitors of RORγt and are useful in the treatment of diseases and conditions mediated by RORγt.

6 Claims, No Drawings

COMPOUNDS

CROSS-REFERENCE TO RELATED APPLICATIONS

The present application is a continuation of, and claims priority to, International Application No. PCT/GB2015/053184, filed Oct. 23, 2015, which claims priority to Great Britain Application No. GB1419015.1, filed Oct. 24, 2014, the contents of all of which are hereby incorporated herein by reference in their entireties.

The present invention relates to compounds which are inhibitors of retinoic acid-related orphan receptor γt (RORγt) activity and which are therefore of use in the treatment of immune-mediated diseases, including autoimmune diseases, and inflammatory conditions. The invention also relates to methods of preparing the compounds and pharmaceutical compositions containing them.

RORγt is known to play a central role in immune system development since it both regulates development of T cells in the thymus and differentiation of effector T cells in the periphery. RORγt is also required for the differentiation of pro-inflammatory Th17 cells (Ivanov et al, *Cell*, 126, 1121-1133, 2006). Small molecule inhibitors of RORγt inhibit the differentiation of human Th17 cells in vitro and reduce Th17 cell numbers and disease activity in animal models of autoimmune disease (Huh et al., 2011, *Nature* 472:486-490). RORγ is also involved in the development of other pathogenic immune cells include type 3 innate lymphoid cells (ILCs). Interleukin 23 activates ILCs in a RORγt-dependent manner (Luci et al., 2008; Buonocore et al., 2010, *Nature* 464:1371-1375) and these cells contribute to experimental colitis and are present in the inflamed intestine of patients with IBD (Buonocore et al., 2010; Geremia et al., 2011, *J Exp Med* 208:1127-1133).

It has been demonstrated that Th17 cells and their products, IL17A, IL-17F, IL-21 and IL-22, are associated with the pathology of various inflammatory and autoimmune disorders, in particular, chronic inflammatory diseases such as psoriasis, rheumatoid arthritis, multiple sclerosis, inflammatory bowel diseases, ankylosing spondylitis, systemic lupus erythematosus and lung diseases including severe asthma, chronic obstructive pulmonary disease and cystic fibrosis.

Some antagonists of RORγt are known and, for example, WO 2012/106995A1, WO 2014/026327, WO 2014/026328, WO 2014/026329, WO 2014/026330, WO 2014/028589, WO 2014/028592, WO 2014/028597 and WO 2014/028600 all relate to compounds which are said to have RORγt inhibiting activity.

The present invention relates to novel antagonists of RORγt which are of use in the treatment and prevention of these and related conditions.

In a first aspect of the present invention there is provided a compound of general formula (I):

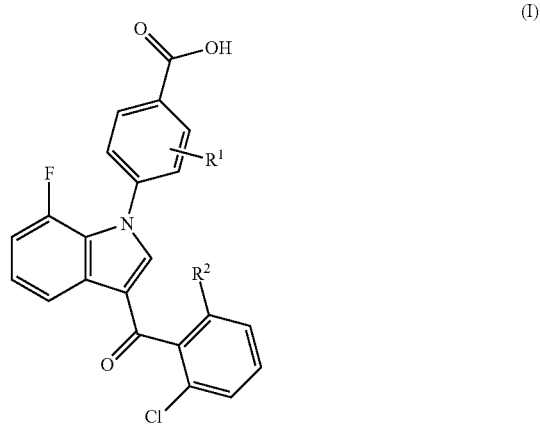

(I)

wherein
$R^1$ is H, F or OH;
$R^2$ is $C_{1-3}$ alkyl, $C_{1-3}$ haloalkyl or cyclopropyl;
provided that when $R^1$ is H, $R^3$ is $C_{1-3}$ haloalkyl;
or a pharmaceutically or veterinarily acceptable salt, solvate or hydrate thereof or a deuterated or tritiated variant thereof, including all stereoisomers.

The compounds of the invention are inhibitors of RORγt and are therefore of use in the treatment and prevention of a number of inflammatory and autoimmune conditions.

WO 2015/087234 relates to RORγt which are very similar to the compounds of the present invention. However, the present inventors have demonstrated that by careful selection of substituents, it is possible to improve the activity of these compounds.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification the term "$C_{1-3}$ alkyl" refers to a fully saturated straight or branched hydrocarbon chain having from 1 to 3 carbon atoms. Examples include methyl, ethyl, n-propyl, isopropyl, t-butyl, n-hexyl.

The term "$C_{3-8}$ cycloalkyl" refers to a fully saturated hydrocarbon ring having from 3 to 8 carbon atoms. Examples include cyclopropyl, cyclopentyl and cyclohexyl.

The term "$C_{1-8}$ haloalkyl" refers to a $C_{1-8}$ alkyl group as defined above in which one or more hydrogen atoms are replaced by halo atoms. Haloalkyl groups may have any number of halo substituents from 1 to perhalosubstituted. Examples include chloromethyl, trifluoromethyl, 1-bromoethyl, 1,1,2,2-tetrafluoroethyl etc.

In the present specification, "halo" refers to fluoro, chloro, bromo or iodo.

The terms "deuterated variant" and "tritiated variant" refer respectively to compounds in which one or more of the hydrogen atoms is a deuterium or is a tritium atom.

Appropriate pharmaceutically and veterinarily acceptable salts of the compounds of general formulae (I) include basic addition salts such as sodium, potassium, calcium, aluminium, zinc, magnesium and other metal salts as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art.

Salts which are not pharmaceutically or veterinarily acceptable may still be valuable as intermediates.

In some suitable compounds of general formula (I), $R^1$ is H.

In other suitable compounds of general formula (I), $R^1$ is F. Suitably, in this case the F is positioned at the 3-position of the phenyl ring (i.e. adjacent to the atom which is linked to the indole ring system).

In yet other suitable compounds of general formula (I), $R^1$ is OH. Suitably the OH is positioned at the 2-position of the phenyl ring (i.e. adjacent to the C(O)OH group).

In the compounds of general formula (I), $R^2$ is suitably $C_{1-2}$ alkyl, $C_{1-2}$ haloalkyl or cyclopropyl.

More suitably, $R^2$ is trifluoromethyl or cyclopropyl, especially trifluoromethyl.

Some particularly suitable compounds of the invention include:

4-{3-[2-chloro-6-(trifluoromethyl)benzoyl]-7-fluoro-1H-indol-1-yl}benzoic acid (Compound 1);
4-[3-[2-chloro-6-(trifluoromethyl)benzoyl]-7-fluoro-1H-indol-1-yl]-2-hydroxy-benzoic acid (Compound 2);
4-[3-[2-chloro-6-(trifluoromethyl)benzoyl]-7-fluoro-1H-indol-1-yl]-3-fluoro-benzoic acid (Compound 3);
4-[3-(2-chloro-6-cyclopropyl-benzoyl)-7-fluoro-1H-indol-1-yl]-3-fluoro-benzoic acid (Compound 4);

$C_{1-6}$ alkyl and benzyl esters thereof; and, their pharmaceutically or veterinarily acceptable salts, solvates or hydrates or a deuterated or tritiated variant thereof, including all stereoisomers.

Compounds of general formula (I) may be prepared from compounds of general formula (II):

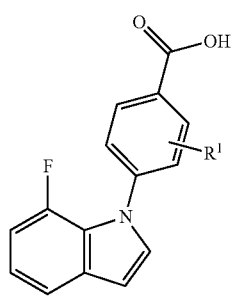

(II)

wherein $R^1$ is as defined for general formula (I);
by reaction with a compound of general formula (III):

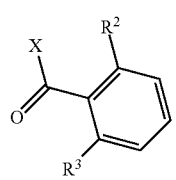

(III)

wherein $R^2$ and $R^3$ are as defined for general formula (I) and X is a leaving group, for example halo and particularly chloro.

The reaction may be conducted in an aqueous solvent and in the presence of a base, which may be, for example, a quaternary nitrogen compound or an organometallic reagent such as dimethylaluminium chloride.

Suitably the reaction will be carried out under an inert atmosphere, for example under nitrogen.

Compounds of general formulae (II) and (III) are known and are readily available or may be prepared by methods known to those of skill in the art.

The compounds of the present invention are useful in the treatment of diseases and conditions mediated by RORγt, in particular inflammatory and autoimmune diseases.

Therefore, in a further aspect of the invention, there is provided a compound of general formula (I) as defined above for use in medicine, particularly for use in the treatment or prevention of diseases and conditions mediated by RORγt, in particular inflammatory and autoimmune diseases.

More specifically, there is provided a compound of general formula (I) as defined above for use in the treatment or prevention of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis. In a further aspect, there is provided the use of a compound of general formula (I) in the preparation of an agent for the treatment or prevention of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis.

In addition, the invention provides a method for the treatment or prevention of a disease or condition selected from the group consisting of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis, the method comprising administering to a patient in need of such treatment and effective amount of a compound of general formula (I).

The compounds of the present invention will generally be administered to a patient in a suitable pharmaceutical formulation. Therefore, in a further aspect of the invention there is provided a pharmaceutical or veterinary composition comprising a compound of general formula (I) together with a pharmaceutically or veterinarily acceptable excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit RORγt.

Compounds of general formula (I) may be used in combination with one or more other active agents which are useful in the treatment of the diseases and conditions listed above. These active agents may be other RORγt inhibitors but will more usually have a different mechanism of action.

Therefore the pharmaceutical composition may also contain one or more of such additional active agents.

There is also provided a combined preparation comprising a compound of formula (I) together with an additional active ingredient, for simultaneous, sequential or separate use in the treatment of a disease or condition mediated by RORγt as described above.

The invention will now be described in greater detail with reference to the following non-limiting examples.

In the examples, the following abbreviations are used.

| | |
|---|---|
| DCM | Dichloromethane |
| DMSO | Dimethylsulfoxide |
| EtOAc | Ethyl acetate |
| FCC | Flash column chromatography |
| LCMS | Liquid chromatography-mass spectrometry |
| MeCN | Acetonitrile |
| rt | Room temperature |
| THF | Tetrahydrofuran |
| tr | Retention time |

General Experimental Details for all Examples Except Comparative Example 1:

Reverse phase HPLC was performed with a Waters FractionLynx system with integrated MS detection. Chromatographic conditions; Gradient 5-95% ACN in 0.1M HCO2H, pH3. Column: Waters Sunfire C18 ODB 5μ 19×150 mm.

Reverse phase HPLC on SCF was performed with a Waters Prep100 SCF system with integrated MS detection. Chromatographic conditions; MeOH/NH3 20 mM, Column: Phenomenex Luna Hilic 5μ, 30×250 mm.

Analytical LC-MS experiments were performed using a Waters Acquity system combined with a Waters Xevo Q-ToF Mass or a Shimadzu 2010EV UPLC system in ESI mode. Chromatographic conditions: gradient 5-90% ACN, pH10. Column: Waters Acquity BEH C18 1.7μ 2.1×50 mm.

NMR spectra were recorded on a Bruker Avance, Avance II or Avance III spectrometer at a proton frequency of 300, 400, 500 or 600 MHz. The central peaks of chloroform-δ (H 7.26 ppm), CD3OD (H 3.30 ppm) or DMSO-d6 (H 2.49 ppm) were used as internal references.

Unless otherwise stated, starting materials were commercially available or previously described in the literature. All solvents and commercial reagents were of laboratory grade and were used as received unless otherwise stated.

Chemical names are preferably IUPAC names which were generated using ACD Labs 2014, or ChemDraw Ultra version 11.0.

General Experimental Details for Comparative Example 1:

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts (δ) are in parts per million.

Analytical HPLC-MS (METCR1673), was performed on Shimadzu LCMS-2010EV systems using reverse phase Supelco Ascentis Express (2.7 μm, 2.1×30 mm), gradient 5-100% B (A=water/0.1% formic acid, B=acetonitrile/0.1% formic acid) over 1.6 minutes injection volume 3 μL, flow=1.0 mL/minute. UV spectra were recorded at 215 nm using a SPD-M20A photo diode array detector. Mass spectra were obtained over the range m/z 100 to 100 at a sampling rate of 2 scans per second using a LCMS2010EV. Data were integrated and reported using Shimadzu LCMS-Solutions andPsiPort software.

Alternatively, (MET-uHPLC-AB-101) analytical HPLC-MS were performed on a Waters Acquity UPLC system with Waters PDA and ELS detectors using a PhenomenexKinetex-XB C-18 column, (1.7 μM, 2.1 mm×100 mm at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynxsoftware.

EXAMPLE 1

Synthesis of 4-[3-[2-chloro-6-(trifluoromethyl)benzoyl]-7-fluoro-1H-indol-1-yl]benzoic acid (Compound 1)

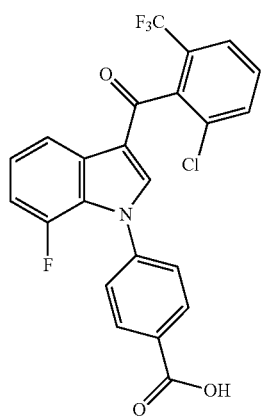 [SMILES: O=C(O)c1ccc(-n2cc(C(=O)c3c(Cl)cccc3C(F)(F)F)c3cccc(F)c32)cc1]

Step 1:

7-fluoro-1H-indole (1.5 g, 11.10 mmol), 4-iodobenzoic acid (2.75 g, 11.10 mmol), 2-methylquinolin-8-ol (0.088 g, 0.55 mmol), copper(I) iodide (0.317 g, 1.66 mmol) were mixed as solids and diluted in DMSO (25 mL). potassium carbonate (4.60 g, 33.30 mmol) was added and the mixture was degassed by bubbling nitrogen for 15 mins. The mixture was stirred at 90° C. for 2 days. The mixture was partitioned between 4 M HCl (45 mL) and ethyl acetate (200 ml). The layers were separated and the organic layer was washed with water (2×10 mL). The organic layer was passed through a phase separator and concentrated under reduced pressure until some 30 mL solvent remained. The mixture was filtered to give the product as a brown solid (1.38 g, 48%).

MS ESI⁻ [M-H]⁻ 254.1

Step 2:

4-(7-fluoro-1H-indol-1-yl)benzoic acid (1.38 g, 5.41 mmol) was mixed with dichloromethane (25 mL) under an atmosphere of nitrogen. dimethylaluminum chloride (10.81 mL, 10.81 mmol) was added slowly while cooling the mixture in an ice bath. 2-chloro-6-(trifluoromethyl)benzoyl chloride (1.051 mL, 6.49 mmol) was added dropwise during 15 mins. The mixture was left for 15 mins with cooling and then quenched by addition of 4M HCl (15 mL). The mixture was partitioned between ethyl acetate (200 mL) and brine (30 ml). 15 mL of THF helped to clear layers. The layers were separated and the organic layer was washed with brine (3×30 mL). The organic layer was passed through a phase separator and concentrated under reduced pressure.

The material was purified by reverse phase HPLC Kromasil C8, 50×250 mm, linear gradient of 35-75% acetonitrile in water/acetonitrile/formic acid (95/5/0.2). The product fractions were pooled and concentrated under reduced pressure. The formed solid was collected by filtration and azeotroped with ethyl actate. The solid was dissolved in refluxing toluene (appr. 40 mL) and the solution was slowly allowed to cool and stirred overnight. The mixture was filtered to give the product as a white solid (0.850 g, 34%).

$^1$H NMR (500 MHz, CD$_2$Cl2) δ 7.11-7.2 (m, 1H), 7.36-7.50 (m, 2H), 7.57-7.66 (m, 3H), 7.73-7.8 (m, 2H), 8.19-8.27 (m, 2H).

Expected Number of Hs: 12

Assigned Hs: 10.

Purity>99%, HRMS (C$_{23}$H$_{12}$ClF$_4$NO$_3$+H), expected 462.0515, observed 462.0504.

COMPARATIVE EXAMPLE 2

Synthesis of 4-[7-fluoro-3-[2-fluoro-6-(trifluoromethyl)benzoyl]-1-H-indol-1-yl]benzoic acid (Comparator Compound 2)

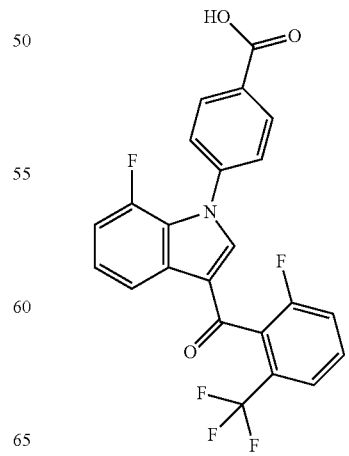

4-([-7-fluoro]-1H-indol-1-yl)benzoic acid (0.11 mmol) was dissolved in dichloromethane (0.5 mL) and dimethylaluminum chloride (1M in hexanes) (0.211 mL, 0.21 mmol) was added. 2-fluoro-4-trifluoromethylbenzoyl chloride (0.21 mmol), dissolved in dichloromethane (0.5 mL), was added and the resulting mixture was stirred at ambient temperature for 30 mins. The mixture was partitioned between 4 M HCl (2 mL) and dichloromethane (5 mL). The water layer was extracted with dichloromethane (2×5 mL) and the combined organic layer was passed through a phase separator. The organic layer was concentrated under reduced pressure. The residue was dissolved in DMSO (1 mL), filtered and purified by reverse phase HPLC to give the product (yield 32%)

1H NMR (600 MHz, DMSO) δ 7.25 (m, 1H), 7.40 (m, 1H), 7.67-7.76 (m, 4H), 7.76-7.82 (m, 1H), 8.02-8.07 (m, 2H), 8.07-8.19 (broad s, 1H), 8.29 (s, 1H).

Expected Number of Hs: 12
Assigned Hs: 11.

EXAMPLE 3

Synthesis of 4-[3-[2-chloro-6-(trifluoromethyl)benzoyl]-7-fluoro-indol-1-yl]-2-hydroxy-benzoic acid (Compound 2)

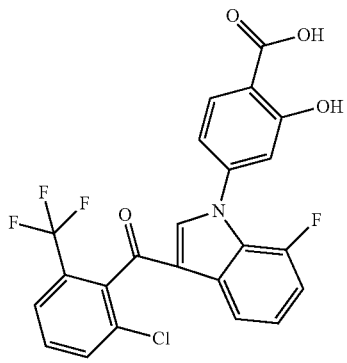 [SMILES: O=C(O)c1ccc(-n2cc(C(=O)c3c(Cl)cccc3C(F)(F)F)c3cccc(F)c32)cc1O]

This compound was made using a method similar to that described above for Comparator Compound 2, yield 36%.

1H NMR (600 MHz, DMSO) δ 6.87 (d, 1H), 6.91 (s, 1H), 7.06 (s, 1H), 7.14 (s, 1H), 7.22 (t, 2H), 7.37 (s, 1H), 7.74 (t, 1H), 7.80 (d, 1H), 7.89 (m, 2H), 8.10 (s, 1H), 8.20.

EXAMPLE 4

Synthesis of 4-[3-[2-chloro-6-(trifluoromethyl)benzoyl]-7-fluoro-indol-1-yl]-3-fluoro-benzoic acid (Compound 3)

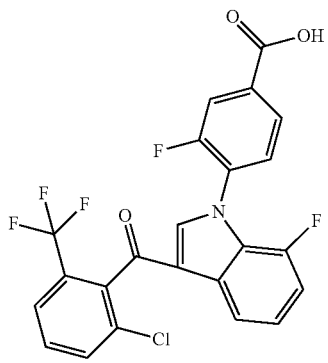 [SMILES: O=C(O)c1ccc(-n2cc(C(=O)c3c(Cl)cccc3C(F)(F)F)c3cccc(F)c32)c(F)c1]

This compound was made using a method similar to that described above for Comparator Compound 2, yield 20%.

1H NMR (600 MHz, DMSO) δ 7.24 (m, 1H), 7.39 (s, 1H), 7.76 (q, 1H), 7.82 (d, 1H), 7.86-7.94 (m, 4H), 8.22 (s, 2H).

Expected Number of Hs: 11
Assigned Hs: 10.

COMPARATIVE EXAMPLE 5

Synthesis of 3-fluoro-4-[7-fluoro-3-[2-fluoro-6-(trifluoromethyl)benzoyl]-1H-indol-1-yl]benzoic acid (Comparator Compound 5)

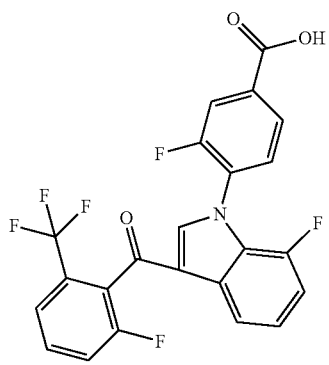 [SMILES: O=C(O)c1ccc(-n2cc(C(=O)c3c(F)cccc3C(F)(F)F)c3cccc(F)c32)c(F)c1]

This compound was made using a similar method to that described above for Comparative Example 2, yield 39%.

$^1$H NMR (600 MHz, DMSO) δ 7.22-7.27 (m, 1H), 7.37-7.43 (m, 1H), 7.7-7.96 (m, 7H), 8.11 (broad s), 8.31 (s, 1H).

EXAMPLE 6

Synthesis of 4-[3-(2-chloro-6-cyclopropyl-benzoyl)-7-fluoro-1H-indol-1-yl]-3-fluoro-benzoic acid (Compound 4)

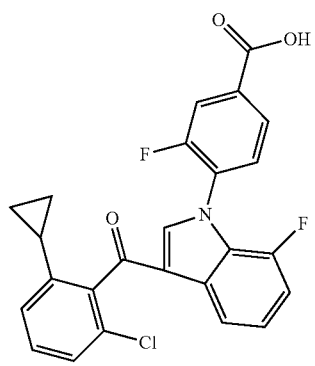 [SMILES: O=C(O)c1ccc(-n2cc(C(=O)c3c(Cl)cccc3C3CC3)c3cccc(F)c32)c(F)c1]

This compound was made using a similar method to that described above for Comparative Example 2, yield 80%.

1H NMR (600 MHz, DMSO) δ 0.64 (d, 1H), 0.76 (m, 2H), 0.82-0.91 (m, 1H), 1.73 (m, 1H), 7.01 (d, 1H), 7.22 (m, 1H), 7.28-7.43 (m, 3H), 7.83 (t, 1H), 7.87-7.94 (m, 2H), 8.04 (s, 2H).

Expected Number of Hs: 16
Assigned Hs: 15.

COMPARATIVE EXAMPLE 7

Synthesis of 4-[3-[2-chloro-6-(trifluoromethyl)benzoyl]-1H-indol-1-yl]benzoic acid (Comparator Compound 1)

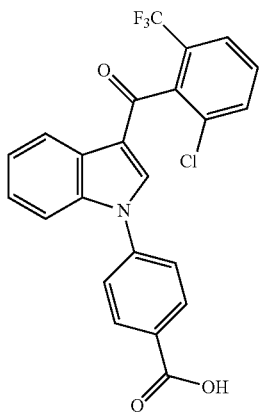 [SMILES: O=C(O)c1ccc(-n2cc(C(=O)c3c(Cl)cccc3C(F)(F)F)c3ccccc32)cc1]

This compound was synthesised using a similar method to that used for Compound 1.

$^1$H NMR (500 MHz, DMSO-d6) δ 13.19 (s, 1H), 8.53-8.18 (m, 2H), 8.15-8.07 (m, 2H), 8.00-7.84 (m, 2H), 7.83-7.62 (m, 4H), 7.41 (s, 2H).

COMPARATIVE EXAMPLE 8

Synthesis of 4-[3-[2-chloro-6-(trifluoromethyl)benzoyl]-1H-indol-1-yl]benzoic Synthesis 4-[3-(2,6-dichlorobenzoyl)-7-fluoro-1H-indol-1-yl]benzoic acid (Comparator Compound 3)

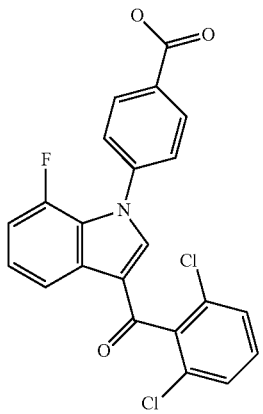 [SMILES: O=C(O)c1ccc(-n2cc(C(=O)c3c(Cl)cccc3Cl)c3cccc(F)c32)cc1]

This compound was made using a method similar to that described above for Compound 2, yield 22%.

1H NMR (600 MHz, DMSO) δ 7.25 (m, 1H), 7.40 (m, 1H), 7.54 (m, 1H), 7.57-7.62 (m, 2H), 7.71 (m, 2H), 8.01-8.15 (m, 2H+hump 1H), 8.23 (s, 1H), 13.23 (s, 1H).

COMPARATIVE EXAMPLE 9

Synthesis of 4-[3-[2-chloro-6-(trifluoromethyl)benzoyl]-1H-indol-1-yl]benzoic Synthesis of 4-[3-(2,6-dichlorobenzoyl)-7-fluoro-1H-indol-1-yl]-3-fluorobenzoic acid (Comparator Compound 4)

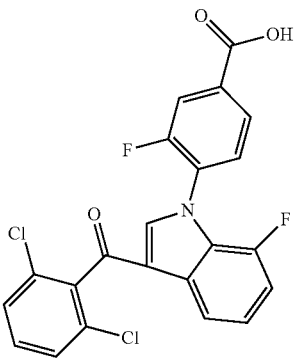 [SMILES: O=C(O)c1ccc(-n2cc(C(=O)c3c(Cl)cccc3Cl)c3cccc(F)c32)c(F)c1]

This compound was made using a method similar to that described above for Compound 2, yield 50%.

1H NMR (600 MHz, DMSO) δ 7.18-7.29 (m, 1H), 7.39 (m, 1H), 7.54 (m, 1H), 7.60 (m, 2H), 7.84 (t, 1H), 7.88 (s, 2H), 8.08 (s, 1H), 8.26 (s, 1H).

Expected Number of Hs: 11
Assigned Hs: 10.

Biological Examples

EXAMPLE 12

FRET Assay

This assay measures the binding of the SRC-1 peptide to the RORγ ligand binding domain in the presence and absence of compound. The SRC-1 peptide was tagged with the streptavidin-europium and the RORγ ligand binding domain was tagged with strepavidin-APC. Labelled RORγ ligand binding domain (50 nM) and SRC-1 peptide (80 nM) were incubated in buffer containing 50 mM MOPS pH7.4, 50 mM potassium fluoride, 50 μM CHAPS (0.003% l), 0.1 mg/ml BSA (0.01%) and 50 mM DTT for 1 hour in the dark at room temperature n the presence and absence of compound.

Inverse agonists of coactivator binding will prevent a proximity based energy transfer between from Eu to APC resulting in decrease in the FRET signal when measured at 665 nM.

Assay Protocol

The assay was run in black 384 well plates (Greiner cat no: 784900). Various concentrations of test ligands in 0.1 microliters DMSO were dispensed to assay plates using an Labcyte Echo acoustic dispenser. Two pre-mixes were prepared and incubated for 1 hr at room temp in the dark. Pre-mix 1 comprised 100 nM Protein (Biotinylated HN-Avi-MBP-TCS-hRORg (258-518)) and 60 nM Streptavidin APC in assay buffer, 50 mM MOPS pH7.4, 50 mM KF, 0.003% (w/v) CHAPS, 10 mM DTT and 0.01% (w/v) BSA and pre-mix 2 comprised 160 nM biotinylated SRC-1 peptide (NCOA1-677-700) and 20 nM Europium-W8044 labelled Streptavidin in assay buffer. Five microliters of pre-mix 2 was dispensed to assay plates containing test compound and incubated for 15 minutes prior to adding five microliters of pre-mix 1. Plates were incubated at room temperature for 1 hour in the dark, prior to reading in a Pherastar multi-mode plate reader using HTRF filter set (ex 320, em 612 and 665). The FRET signal at 665 nM was divided by the signal at 612 nM and multiplied by 10,000 to generate a signal ratio value for each well. The raw data was transformed to % effect using the equation:

Compound % effect=100*[(X−min)/(max−min)], where X represents the normalized value for the compound based on the Min (vehicle) and Max (reference compound) inhibition control.

The concentration of test ligand that inhibited the activity by 50% (i.e., the $IC_{50}$) was calculated by plotting the % effect versus test ligand concentration and fitting the data using the Genedata Screener Smart fit algorithm.

The results for Compounds 1-14 are shown in Table 1.

TABLE 1

Mean $IC_{50}$ values for compounds in RORγ FRET assay

| Compound No | RORγ FRET - Mean $IC_{50}$ (nM) |
|---|---|
| 1 | 43.62 |
| 2 | 17.92 |
| 3 | 37.86 |
| 4 | 42.94 |
| Comparator 1 | 97.4 |
| Comparator 2 | 61.92 |
| Comparator 3 | 91.63 |
| Comparator 4 | 59.61 |
| Comparator 5 | 110.7 |

EXAMPLE 13

Human Th17 Cell Differentiation Assay

Human CD4+CCR6+ T cells were isolated from peripheral blood mononuclear cells by positive selection. These cells were incubated in a cocktail of cytokines (1 ng/mL TGF-β1, 10 ng/mL IL-1β, 50 ng/mL IL-23, 10 ng/mL IL-6 and 5 ng/mL IL-2) and antiCD2/CD3/28 beads to induce polarisation and expansion of CD4+ IL-17+ T cells ($T_H17$ cells) over a period of 4 days in the presence and absence of compound.

The concentration of IL17A were measured in the extracellular media by sandwich ELISA. Compounds that inhibited $T_H17$ cell differentiation and expansion reduced the levels of IL-17A in the extracellular media.

The results are shown in Table 2.

TABLE 2

Mean $IC_{50}$ values for compounds in $T_H17$ cell differentiation assay

| Compound No | Inhibition of $T_H17$ cell differentiation - Mean $IC_{50}$ (nM) |
|---|---|
| 1 | 19.79 |
| 2 | 12.59 |
| 3 | 15.04 |
| 4 | 31.9 |
| Comparator 1 | 45.31 |
| Comparator 2 | 48.22 |
| Comparator 3 | 90.77 |
| Comparator 4 | 71.31 |
| Comparator 5 | 47 |

Several conclusions can be drawn from the results presented in Tables 1 and 2.

As can be seen from a comparison of the results for Compound 1 and Comparator Compound 1, the presence of the F at the 7-position of the indole ring greatly increases the activity.

Furthermore, compounds in which $R^2$ is trifluoromethyl are significantly more active than similar compounds in which there is a chloro at this position. This can be seen from a comparison of the results for Compound 1 with those for Comparator Compound 3 or the results for Compound 3 with those for Comparator Compound 4 Compounds in which $R^2$ is cyclopropyl are also more active than compounds with a chloro in this position as shown by comparing the results for Compound 4 with those for Comparator Compound 4.

Compounds of the present invention which have a chloro group at the 2-position of the ring attached to the indole 3-position are more active than compounds with a fluoro group in this position. This can be seen from a comparison of the results for Compound 1 with those of Comparator Compound 2 or the results for Compound 3 with those for Comparator Compound 5.

EXAMPLE 14

Oral Pharmacokinetics in Rats

Compound 1 was administered to rats intravenously at a dose of 0.47 mg/kg and orally at a dose of 2.5 mg/kg. Compound 1 was well absorbed after oral administration (F %=61%) and had achieved high plasma levels (Cmax=1.8 μM). The plasma concentrations were sustained for several hours ($t_{1/2}$ after intravenous administration was 5.1 hours and $t_{1/2}$ after oral administration was 6.4 hours).

The invention claimed is:

1. A pharmaceutical composition comprising a pharmaceutically or veterinarily acceptable excipient and a compound of formula (I):

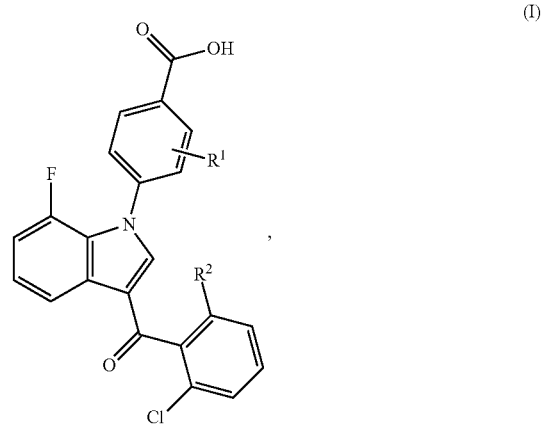

wherein:
$R^1$ is selected from the group consisting of H, F and OH;
$R^2$ is selected from the group consisting of $C_{1-3}$ alkyl, $C_{1-3}$ haloalkyl and cyclopropyl;
provided that, when $R^1$ is H, $R^2$ is $C_{1-3}$ haloalkyl;
or a pharmaceutically or veterinarily acceptable salt, solvate or hydrate thereof, a deuterated or tritiated derivative thereof, or a stereoisomer thereof;

wherein the pharmaceutical composition is orally bioavailable.

2. The pharmaceutical composition of claim 1, wherein in (I) R¹ is H.

3. The pharmaceutical composition of claim 1 wherein in (I) R² is trifluoromethyl.

4. A pharmaceutical composition comprising a pharmaceutically acceptable excipient and 4-{3-[2-chloro-6-(trifluoromethyl) benzoyl]-7-fluoro-1H-indol-1-yl}benzoic acid (Compound 1), or a pharmaceutically or veterinarily acceptable salt, solvate or hydrate thereof, a deuterated or tritiated derivative thereof, or a stereoisomer thereof wherein the pharmaceutical composition is orally bioavailable.

5. A method of treating a disease or condition mediated by RORγt, the method comprising administering orally to a patient in need of such treatment a pharmaceutical composition comprising a pharmaceutically or veterinarily acceptable excipient and a compound of formula (I):

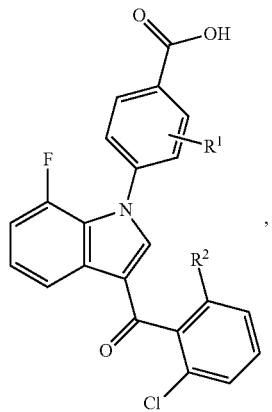

(I)

wherein:
R¹ is selected from the group consisting of H, F and OH;
R² is selected from the group consisting of $C_{1-3}$ alkyl, $C_{1-3}$ haloalkyl and cyclopropyl;
provided that, when R¹ is H, R² is $C_{1-3}$ haloalkyl;

or a pharmaceutically or veterinarily acceptable salt, solvate or hydrate thereof, a deuterated or tritiated derivative thereof, or a stereoisomer thereof;
wherein the pharmaceutical composition is orally bioavailable, and
wherein the disease or condition mediated by RORγt is at least one selected from the group consisting of asthma, chronic obstructive pulmonary disease (COPD), bronchitis, allergic diseases, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease, and scleritis.

6. A method of treating a disease or condition mediated by RORγt, the method comprising administering orally to a patient in need of such treatment a pharmaceutical composition comprising a pharmaceutically acceptable excipient and 4-{3-[2-chloro-6-(trifluoromethyl) benzoyl]-7-fluoro-1H-indol-1-yl}benzoic acid (Compound 1), or a pharmaceutically or veterinarily acceptable salt, solvate or hydrate thereof, a deuterated or tritiated derivative thereof, or a stereoisomer thereof;
wherein the pharmaceutical composition is orally bioavailable, and
wherein the disease or condition mediated by RORγt is at least one selected from the group consisting of asthma, chronic obstructive pulmonary disease (COPD), bronchitis, allergic diseases, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease, and scleritis.

* * * * *